United States Patent
Lachaine et al.

(10) Patent No.: US 10,542,962 B2
(45) Date of Patent: Jan. 28, 2020

(54) ADAPTIVE RADIOTHERAPY TREATMENT USING ULTRASOUND

(75) Inventors: Martin Lachaine, Montreal (CA); Sebastien Tremblay, St. Jean-Sur-Richelieu (CA); Philippe Fortier, St.-Jean-Sur-Richelieu (CA); Sergei Koptenko, Verdun (CA); Tony Falco, La Prairie (CA)

(73) Assignee: Elekta, LTD, Montreal, Quebec (CA)

( * ) Notice: Subject to any disclaimer, the term of this patent is extended or adjusted under 35 U.S.C. 154(b) by 1190 days.

(21) Appl. No.: 12/831,546

(22) Filed: Jul. 7, 2010

(65) Prior Publication Data

US 2011/0009742 A1 Jan. 13, 2011

Related U.S. Application Data

(60) Provisional application No. 61/224,582, filed on Jul. 10, 2009.

(51) Int. Cl.
*A61B 8/00* (2006.01)
(52) U.S. Cl.
CPC .................. *A61B 8/4245* (2013.01)
(58) Field of Classification Search
CPC ....... A61B 6/4225; A61B 6/4441; A61B 8/08; A61B 8/085; A61B 8/42; A61B 8/4227; A61B 8/4245; A61B 8/4472; A61B 8/483; A61N 2005/1058; A61N 5/1049; A61N 5/1067
USPC .................. 600/437, 439; 382/128
See application file for complete search history.

(56) References Cited

U.S. PATENT DOCUMENTS

| | | | |
|---|---|---|---|
| 3,082,322 A | 3/1963 | Koerner et al. | |
| 3,777,124 A | 12/1973 | Pavkovich | |
| 3,987,281 A | 10/1976 | Hodes | |
| 3,991,310 A | 11/1976 | Morrison | |
| 4,118,631 A | 10/1978 | Froggatt | |
| 4,618,978 A | 10/1986 | Cosman | |
| 4,882,741 A | 11/1989 | Brown | |
| 4,923,459 A | 5/1990 | Nambu | |
| 4,943,990 A | 7/1990 | Schar | |

(Continued)

FOREIGN PATENT DOCUMENTS

| | | |
|---|---|---|
| CA | 2416887 A1 | 2/2002 |
| CA | 2621741 A1 | 3/2007 |

(Continued)

OTHER PUBLICATIONS

Wu et al., "Effect of Ultrasound Probe on Dose Delivery During Real-time Ultrasound-Guided Tumor Tracking", Proceedings of the 28th IEEE EMBS Annual International Conference, New York City, USA, Aug. 30-Sep. 3, 2006, pp. 3799-3802.*

(Continued)

*Primary Examiner* — Katherine L Fernandez
(74) *Attorney, Agent, or Firm* — Schwegman Lundberg & Woessner, P.A.; Sanjay Agrawal

(57) ABSTRACT

Radiation treatment is delivered to a patient by positioning the patient such that a radiation beam is delivered to a lesion within the patient along a beam-delivery path while securing a diagnostic imaging device about the patient such that the diagnostic imaging device does not intersect the beam-delivery path. Radiation therapy is simultaneously delivered along the beam-delivery path while diagnostic images are obtained using the imaging device.

16 Claims, 6 Drawing Sheets

(56) References Cited

U.S. PATENT DOCUMENTS

| | | | |
|---|---|---|---|
| 5,039,867 | A | 8/1991 | Nishihara et al. |
| 5,080,100 | A | 1/1992 | Trotel |
| 5,086,401 | A | 2/1992 | Glassman et al. |
| 5,099,846 | A | 3/1992 | Hardy |
| 5,107,839 | A | 4/1992 | Houdek et al. |
| 5,117,829 | A | 6/1992 | Miller et al. |
| 5,138,647 | A | 8/1992 | Nguyen et al. |
| 5,207,223 | A | 5/1993 | Adler |
| 5,222,499 | A | 6/1993 | Allen et al. |
| 5,233,990 | A | 8/1993 | Barnea |
| 5,291,889 | A | 3/1994 | Kenet et al. |
| 5,295,483 | A | 3/1994 | Nowacki et al. |
| 5,299,288 | A | 3/1994 | Glassman et al. |
| 5,301,674 | A | 4/1994 | Erikson et al. |
| 5,379,642 | A | 1/1995 | Reckwerdt et al. |
| 5,389,101 | A | 2/1995 | Heilbrun et al. |
| 5,391,139 | A | 2/1995 | Edmundson |
| 5,397,329 | A | 3/1995 | Allen |
| 5,408,101 | A | 4/1995 | Wong |
| 5,411,026 | A | 5/1995 | Carol |
| 5,438,991 | A | 8/1995 | Yu et al. |
| 5,442,675 | A | 8/1995 | Swerdloff et al. |
| 5,446,548 | A | 8/1995 | Gerig et al. |
| 5,447,154 | A | 9/1995 | Cinquin et al. |
| 5,483,961 | A | 1/1996 | Kelly et al. |
| 5,511,549 | A | 4/1996 | Legg et al. |
| 5,524,627 | A | 6/1996 | Passi |
| 5,531,227 | A | 7/1996 | Schneider |
| 5,531,520 | A | 7/1996 | Grimson et al. |
| 5,553,618 | A | 9/1996 | Suzuki et al. |
| 5,591,983 | A | 1/1997 | Yao |
| 5,603,318 | A | 2/1997 | Heilbrun et al. |
| 5,609,485 | A | 3/1997 | Bergman et al. |
| 5,645,066 | A | 7/1997 | Gandini et al. |
| 5,673,300 | A | 9/1997 | Reckwerdt et al. |
| 5,690,108 | A | 11/1997 | Chakeres |
| 5,715,166 | A | 2/1998 | Besl et al. |
| 5,734,384 | A | 3/1998 | Yanof et al. |
| 5,740,225 | A | 4/1998 | Nabatame |
| 5,754,623 | A | 5/1998 | Seki |
| 5,757,881 | A | 5/1998 | Hughes |
| 5,778,043 | A | 7/1998 | Cosman |
| 5,810,007 | A | 9/1998 | Holupka et al. |
| 5,836,954 | A | 11/1998 | Heilbrun et al. |
| 5,851,183 | A | 12/1998 | Bucholz |
| 5,859,891 | A | 1/1999 | Hibbard |
| 5,871,445 | A | 2/1999 | Bucholz |
| 5,952,577 | A | 9/1999 | Passi |
| 5,991,703 | A | 11/1999 | Kase |
| 6,019,724 | A * | 2/2000 | Gronningsaeter et al. ... 600/439 |
| 6,038,283 | A | 3/2000 | Carol et al. |
| 6,094,508 | A | 7/2000 | Acharya et al. |
| 6,106,470 | A | 8/2000 | Geiser et al. |
| 6,112,341 | A | 9/2000 | Moreland |
| 6,117,081 | A | 9/2000 | Jago et al. |
| 6,118,848 | A | 9/2000 | Reiffel |
| 6,119,033 | A | 9/2000 | Spigelman et al. |
| 6,122,341 | A | 9/2000 | Butler et al. |
| 6,129,670 | A * | 10/2000 | Burdette et al. ............ 600/427 |
| 6,138,495 | A | 10/2000 | Paltieli et al. |
| 6,144,875 | A | 11/2000 | Schweikard et al. |
| 6,146,390 | A | 11/2000 | Heilbrun et al. |
| 6,198,957 | B1 | 3/2001 | Green |
| 6,208,883 | B1 | 3/2001 | Holupka et al. |
| 6,254,538 | B1 * | 7/2001 | Downey et al. ............ 600/439 |
| 6,259,943 | B1 | 7/2001 | Cosman et al. |
| 6,269,143 | B1 | 7/2001 | Tachibana |
| 6,285,805 | B1 | 9/2001 | Gueziec |
| 6,292,578 | B1 | 9/2001 | Kalvin |
| 6,307,914 | B1 | 10/2001 | Kunieda et al. |
| 6,314,310 | B1 | 11/2001 | Ben-Haim et al. |
| 6,325,758 | B1 | 12/2001 | Carol et al. |
| 6,345,114 | B1 | 2/2002 | Mackie et al. |
| 6,359,959 | B1 | 3/2002 | Butler et al. |
| 6,366,798 | B2 | 4/2002 | Green |
| 6,385,286 | B1 | 5/2002 | Fitchard et al. |
| 6,385,288 | B1 | 5/2002 | Kanematsu |
| 6,390,982 | B1 | 5/2002 | Bova et al. |
| 6,405,072 | B1 | 6/2002 | Cosman |
| 6,423,009 | B1 | 7/2002 | Downey et al. |
| 6,438,202 | B1 | 8/2002 | Olivera et al. |
| 6,459,769 | B1 | 10/2002 | Cosman |
| 6,491,702 | B2 | 12/2002 | Heilbrun et al. |
| 6,511,430 | B1 | 1/2003 | Sherar et al. |
| 6,516,046 | B1 | 2/2003 | Frohlich et al. |
| 6,535,574 | B1 | 3/2003 | Collins et al. |
| 6,546,073 | B1 | 4/2003 | Lee |
| 6,553,152 | B1 | 4/2003 | Miller et al. |
| 6,560,311 | B1 | 5/2003 | Shepard et al. |
| 6,567,684 | B1 | 5/2003 | Chenevert et al. |
| 6,585,651 | B2 | 7/2003 | Nolte et al. |
| 6,591,127 | B1 | 7/2003 | McKinnon |
| 6,600,810 | B1 | 7/2003 | Hughes |
| 6,621,889 | B1 | 9/2003 | Mostafavi |
| 6,628,983 | B1 | 9/2003 | Gagnon |
| 6,631,284 | B2 | 10/2003 | Nutt et al. |
| 6,636,622 | B2 | 10/2003 | Mackie et al. |
| 6,641,539 | B2 | 11/2003 | Hirooka et al. |
| 6,661,870 | B2 | 12/2003 | Kapatoes et al. |
| 6,662,036 | B2 | 12/2003 | Cosman |
| 6,669,635 | B2 | 12/2003 | Kessman et al. |
| 6,683,985 | B1 | 1/2004 | Kase et al. |
| 6,690,965 | B1 | 2/2004 | Riaziat et al. |
| 6,714,627 | B1 | 3/2004 | Brown et al. |
| 6,725,079 | B2 | 4/2004 | Zuk et al. |
| 6,728,424 | B1 | 4/2004 | Zhu et al. |
| 6,731,970 | B2 | 5/2004 | Schlossbauer et al. |
| 6,750,873 | B1 | 6/2004 | Bernardini et al. |
| 6,754,374 | B1 | 6/2004 | Miller et al. |
| 6,785,409 | B1 | 8/2004 | Suri |
| 6,804,548 | B2 | 10/2004 | Takahashi et al. |
| 6,842,502 | B2 | 1/2005 | Jaffray et al. |
| 6,914,959 | B2 | 7/2005 | Bailey et al. |
| 6,915,008 | B2 | 7/2005 | Barman et al. |
| 6,968,224 | B2 | 11/2005 | Kessman et al. |
| 6,980,679 | B2 | 12/2005 | Jeung et al. |
| 7,092,109 | B2 | 8/2006 | Satoh et al. |
| 7,095,823 | B2 | 8/2006 | Topolnjak et al. |
| 7,260,426 | B2 | 8/2007 | Schweikard et al. |
| 7,333,644 | B2 | 2/2008 | Jerebko et al. |
| 7,343,030 | B2 | 3/2008 | Sawyer |
| 7,430,321 | B2 | 9/2008 | Okada et al. |
| 7,438,685 | B2 | 10/2008 | Burdette et al. |
| 7,535,411 | B2 | 5/2009 | Falco |
| 7,613,501 | B2 | 11/2009 | Scherch |
| 7,634,304 | B2 | 12/2009 | Falco et al. |
| 7,662,097 | B2 * | 2/2010 | Falco et al. .................. 600/437 |
| 7,672,705 | B2 | 3/2010 | Lachaine et al. |
| 7,729,744 | B2 | 6/2010 | Falco et al. |
| 7,801,349 | B2 | 9/2010 | Wang et al. |
| 8,042,209 | B2 | 10/2011 | D'Souza et al. |
| 8,232,535 | B2 | 7/2012 | Olivera et al. |
| 2001/0035871 | A1 | 11/2001 | Bieger et al. |
| 2001/0049475 | A1 | 12/2001 | Bucholz et al. |
| 2002/0018588 | A1 | 2/2002 | Kusch |
| 2002/0065461 | A1 | 5/2002 | Cosman |
| 2002/0082494 | A1 | 6/2002 | Balloni et al. |
| 2002/0087101 | A1 | 7/2002 | Barrick et al. |
| 2002/0122530 | A1 | 9/2002 | Erbel et al. |
| 2002/0156375 | A1 | 10/2002 | Kessman et al. |
| 2002/0176541 | A1 | 11/2002 | Schubert et al. |
| 2002/0183610 | A1 | 12/2002 | Foley et al. |
| 2002/0188194 | A1 | 12/2002 | Cosman |
| 2003/0018232 | A1 | 1/2003 | Elliott et al. |
| 2003/0028401 | A1 | 2/2003 | Kaufman et al. |
| 2003/0112922 | A1 | 6/2003 | Burdette et al. |
| 2003/0135115 | A1 * | 7/2003 | Burdette et al. ............ 600/437 |
| 2003/0144813 | A1 | 7/2003 | Takemoto et al. |
| 2003/0153825 | A1 | 8/2003 | Mooradian et al. |
| 2003/0182072 | A1 | 9/2003 | Satoh et al. |
| 2003/0231790 | A1 | 12/2003 | Bottema |
| 2004/0015075 | A1 | 1/2004 | Kimchy et al. |
| 2004/0015176 | A1 | 1/2004 | Cosman |
| 2004/0034301 | A1 * | 2/2004 | Falco ......................... 600/427 |

(56) References Cited

U.S. PATENT DOCUMENTS

| | | | |
|---|---|---|---|
| 2004/0092815 A1 | 5/2004 | Schweikard et al. | |
| 2004/0146137 A1 | 7/2004 | Bruder et al. | |
| 2004/0176925 A1 | 9/2004 | Satoh et al. | |
| 2004/0184646 A1 | 9/2004 | Oosawa | |
| 2004/0252870 A1 | 12/2004 | Reeves et al. | |
| 2004/0260142 A1 | 12/2004 | Lovoi | |
| 2005/0020917 A1 | 1/2005 | Scherch | |
| 2005/0180544 A1 | 8/2005 | Sauer et al. | |
| 2005/0182316 A1* | 8/2005 | Burdette et al. | 600/424 |
| 2005/0251029 A1* | 11/2005 | Khamene et al. | 600/427 |
| 2006/0020195 A1 | 1/2006 | Falco et al. | |
| 2006/0074292 A1 | 4/2006 | Thomson et al. | |
| 2006/0093205 A1 | 5/2006 | Bryll et al. | |
| 2006/0120608 A1 | 6/2006 | Luo et al. | |
| 2006/0241443 A1 | 10/2006 | Whitmore et al. | |
| 2006/0285641 A1 | 12/2006 | Scherch | |
| 2006/0293583 A1 | 12/2006 | Saracen et al. | |
| 2007/0015991 A1* | 1/2007 | Fu et al. | 600/407 |
| 2007/0038058 A1 | 2/2007 | West et al. | |
| 2007/0055090 A1 | 3/2007 | Neustadter et al. | |
| 2008/0021300 A1* | 1/2008 | Allison | 600/407 |
| 2008/0039713 A1 | 2/2008 | Thomson et al. | |
| 2008/0064953 A1 | 3/2008 | Falco et al. | |
| 2008/0219405 A1 | 9/2008 | Falco et al. | |
| 2008/0292194 A1 | 11/2008 | Schmidt et al. | |
| 2009/0003523 A1 | 1/2009 | Raanes et al. | |
| 2009/0003528 A1 | 1/2009 | Ramraj et al. | |
| 2009/0093716 A1 | 4/2009 | Deischinger et al. | |
| 2009/0110145 A1 | 4/2009 | Lu et al. | |
| 2011/0069815 A1 | 3/2011 | Nord et al. | |

FOREIGN PATENT DOCUMENTS

| | | |
|---|---|---|
| EP | 0647457 A1 | 4/1995 |
| EP | 951697 A1 | 10/1999 |
| EP | 1304960 A1 | 5/2003 |
| EP | 1426806 A2 | 6/2004 |
| EP | 1757228 A1 | 2/2007 |
| EP | 2451355 A1 | 5/2012 |
| EP | 2451355 B1 | 10/2018 |
| FR | 2778574T A1 | 11/1999 |
| JP | 2003-117010 A | 4/2003 |
| JP | 2006000220 A | 1/2006 |
| WO | WO-19992074 A1 | 1/1999 |
| WO | WO-9906644 A1 | 2/1999 |
| WO | WO-9926534 A1 | 6/1999 |
| WO | WO-9927839 A2 | 6/1999 |
| WO | WO-200105316 A1 | 1/2001 |
| WO | WO-200209588 A1 | 2/2002 |
| WO | WO-03039370 A1 | 5/2003 |
| WO | WO-2003039370 | 5/2003 |
| WO | WO-03076003 A2 | 9/2003 |
| WO | WO 2004/033041 A1 | 4/2004 |
| WO | WO-2006051523 A2 | 5/2006 |
| WO | WO-2007028237 A1 | 3/2007 |
| WO | WO-2011003202 A1 | 11/2011 |

OTHER PUBLICATIONS

Hsu et al., "Feasibility of using ultrasound for real-time tracking during radiotherapy", Medical Physics, vol. 32, No. 6, Jun. 2005, pp. 1500-1512.*

Griffiths et al., "Transperineal Ultrasound for Measurement of Prostate Volume: Validation Against Transrectal Ultrasound", The Journal of Urology, vol. 178, Oct. 2007, pp. 1375-1380.*

Pito, A Registration Aid, International Conference on Recent Advanced in 3D Digital Imaging and Modelling, pp. 85-92 (1997).

Pollack et al., Conventional vs. Conformal Radiotherapy for Prostate Cancer: Preliminary Results of Dosimetry and Acute Toxicity, Int. J. Radiation Oncology Biol. Phys., 34(3):555-564.

Robb, Three-Dimensional Visualization in Medicine and Biology. Book Chapter in: Handbook of Medical Imaging: Processing and Analysis, ed. Isaac N. Bankman, Academic Press, San Diego, CA, Chapter 42, pp. 685-671 (2000).

Robinson, Advances in Multi-Modal Data Analysis: The Analyze Software Environment, htt1p:/www.ii.metu.edu.tr/~med-ii/makaleler/analyze_<http://www.ii.metu.edu.tri/~med-ii/makaleler/analyze>sw_enve.pdf, 5 pages. Downloaded on Aug. 10, 2004.

Soffen E.M. et al. Conformal static field radiation therapy treatment of early prostate cancer versus non-conformal techniques: A reduction in acute morbidity. Int J Radiat Oncol Biol Phys, 24: 485-488 (1992).

Thayananthan, A. et al., <http://mi.eng.cam.ac.uk/~bdrs2/papers/thayanantan>cvpr03.pdf, pp. 1-8. Downloaded from the Internet on Aug. 10, 2004.

Tome et al., Commissioning and Quality Assurance of an Optically Guided Three-dimensional Ultrasound Target Localization System for Radiotherapy, Med. Phys., 29(8):1781-1788 (2002).

Zhang, Iterative Point Matching for Registration of Free-Form Curves and Surfaces, International Journal of Computer Vision, 13(2):119-152 (1994).

http/www.ucsfedu/ipouliot/Course,/chapter5.htm.

http://www.acmp.orgimeetings/hershey 2001/hiphlights/benedict pdf.

http://www.ucsfedu/'Jpouliot/Course/Lesson22.htm.

http://www.gemedicalsystems.corri/patient/see treat/positioning.html.

http://www.emoryradiationoncology.org/high-technology.htm.

http://www.ucsfedu/jpouliot/Course/conforrnal_radiation_therapy.htm.

International Search Report for International application No. PCT/CA2007/001626 dated Jan. 3, 2008 (4 pages).

Written Opinion of the International Searching Authority for International application No. PCT/CA2007/001626 dated Dec. 21, 2007 (7 pages).

Supplementary European Search Report dated Oct. 25, 2010 (5 pages).

Besl et al., A Method for Registration of 3d Shapes, IEEE Transactions on Pattern Analysis and Machine Intelligence 14(2):239-256 (1992).

Booth, Modelling, The impact of treatment uncertainties in radiotherapy, University of Adelaide, Mar. 2002), Section 2.4 (http://thesis.library.adelaide.edu.au/uploads/approved/adt-SUA20020816.175301/public/03 chapter2.pdf.

Brujic et al., Analysis of Free-Form Surface Registration, International Conference on Image Processing, pp. 393-396 (1996).

Cuisenaire, O., http)/www.tele.ucl.ac.be/PEOPLE/OC/these/node74.html. <http://www.tele.ucl.ac.be/PEOPLE/OC/these/node74.html,> Posted Oct. 5, 1999, Downloaded from the Internet on Aug. 10, 2004.

Cuisenaire, O., <http://www.tele.ucl.ac.be/PEOPLE/OC/these/node75.html,> Posted Oct. 5, 1999, Downloaded from the Internet on Aug. 10, 2004.

Cuisenaire, O., <http://www.tele.uci.ac.be/PEOPLE/OC/these/node12.html,> Posted Oct. 5, 1999, Downloaded from the Internet on Aug. 10, 2004.

Dubois et al. Intraobserver and Interobserver Variability of MR Imaging- and CT-derived Prostate Volumes after Transperineal Interstitial Permanent Prostate Brachytherapy, Radiology. 207(3):785-9 (1998).

Eggert et al., Simultaneous Registration of Multiple Range Views for Reverse Engineering, International Conference of Pattern Recognition, pp. 243-247 (1996).

Hanks, et al. , Three Dimensional Conformal External Beam Treatment of Prostate Cancer http://prostate-help.org/download/pilgrim/10rad.pdf.

Hanks, et al.,Clinical and Biochemical Evidence of Control of Prostate Cancer at 5 Years After External Beam Radiation, The Journal of Urology, vol. 154, 456-459 (1995).

Haralick et al., Pose Estimation From Corresponding Data Point, IEEE Transactions on Systems, Man, and Cybernetics, 19(6):1426-1446 (1989).

Hua et al., Development of a Semi-Automatic Alignment Tool for Accelerated Localization of the Prostate, Int. J. Radiation Oncology Biol. Phys., 55(3):811-823 (2003).

(56) References Cited

OTHER PUBLICATIONS

Jiang et al., A New Approach to 3-d Registration of Multimodality Medical Images by Surface Matching, SPIE vol. 1808 Visualization in Biomedical Computing pp. 196-213 (1992).
Krempien et al., Daily patient set-up control in radiation therapy by coded light projection, 3 pages.
Michalski et al., Three-Dimensional Conformal Radiation Therapy (3DCRT) for Prostate Cancer, Radiation Oncology Center, Mallinckrodt Institute of Radiology, Washington University Medical Center, St. Louis, Missouri (1996) http://www.phoenix5 org/Infolink/Michalski/#3.
Paskalev et al., Daily Target Localization for Prostate Patients based on 3-D Image Correlation, Phys. Med. Biol., vol. 49, pp. 931-939 (2004).
Pennec et al,. A Framework for Uncertainty and Validation of 3-D Registration Methods Based on Points and Frames, International Journal of Computer Vision 25(3), 203-229 (1997).
Aoki, Y. et al. An *Integrated Radiotherapy Treatment System and its Clinical Application,* Radiation Medicine, vol. 5, No. 4, pp. 131-141, 1987.
Barratt, Dean C., "Accuracy of an Electromagnetic Three-Dimensional Ultrasound System for Carotid Artery Imaging" from Ultrasound in Medicine and Biology, vol. 27, No. 10, 2001, pp. 1421-1425.
Bijhold, J. et al. Fast evaluation of patient set-up during radiotherapy by aligning features in portal and simulator images, Phys. Med. Biol., 1999, vol. 36, No. 12, pp. 1665-1679.
Bijhold, J. *Three-dimensional verification of patient placement during radiotherapy using portal images,* Med. Phys. 20 (2), Pt. 1, Mar./Apr. 1993. pp. 347-356.
Boctor, et al., A Rapid Calibration Method for Registration and 3D Tracking of Ultrasound Images Using Spatial Localizer, Proceedings of the SPIE (2003).
Boyer, A. A review of electronic portal imaging devices (EPIDs), Med. Phys. 19 (1), Jan./Feb. 1992 pp. 1-.
Brigger, et al., "B-Spline Snakes: A Flexible Tool for Parametric Contour Detection," IEEE Transactions on Image Processing, vol. 9, No. 9, Sep. 2000, pp. 1484-1496.
Brunie L. et al. Pre-and intra-irradiation multimodal image registration: principles and first experiments, Radiotherapy and Oncology 29 (1993) pp. 244-252.
Christensen G. E., Inverse consistent registration with object boundary constraints, Biomedical Imaging: Macro to Nano, 2004, IEEE International Symposium on Arlington, VA, USA Apr. 15-18, 2004, Piscataway, NJ, USA, IEEE (4 pages).
Claim Chart for Claim 10 of U.S. Pat. No. 5,447,154.
Cuadra, M.B. et al., Atlas-based Segmentation of pathological MR brain images using a model of lesion growth; Medical Imaging IEEE Transactions on, vol. 23, No. 10, pp. 1301-1314, Oct. 2004.
Czarnota G.J. et al. *Ultrasound imaging of apoptosis: high-resolution non-invasive monitoring of programmed cell death in vitro, in situ and in vivo,* British Journal of Cancer (1999) 81(3), pp. 520-527.
European Search Report for PCT/CA2007/001626 dated Nov. 5, 2010 (6 pages).
http://www.varian.com/pinf/imr000c.html.
http://www.ucsf/edu/jpouliot/Course/conformal_radiation_therapy.htm.
International Preliminary Report on Patentability for International Application No. PCT/CA2005/001106 dated Jan. 23, 2007.
International Preliminary Report on Patentability for PCT/CA2005/001428 dated Oct. 3, 2007 (1 page).
International Search Report and Written Opinion for International Application No. PCT/CA2010/002008 dated May 2, 2012, 7 pages.
International Search Report and Written Opinion for PCT/CA2009/000750, dated Sep. 18, 2009 (8 pages).
International Search Report and Written Opinion of the International Searching Authority for PCT/CA2010/002008 dated Mar. 14, 2011 (7 pages).
International Search Report for PCT/CA2005/001106 dated Nov. 15, 2005.
International Search Report for PCT/CA2005/001428 dated Nov. 16, 2005.
International Search Report for PCT/CA2005/01105 dated Oct. 27, 2005.
International Search Report for PCT/CA2006/001289 dated Oct. 30, 2006 (3 pages).
International Search Report for PCT/CA2006/001461 dated Nov. 30, 2006 (5 pages).
International Search Report for PCT/CA2007/000898 dated Jul. 12, 2007 (3 pages).
Le Verre, C. et al. *Intensity-Based Registration of Portal Images for Patient Positioning in Radiotherapy.*
Leszczynski K W et al., "An Image Registration scheme applied to verification of radiation therapy" British Journal of Radiology British Inst. Radiol UK [Online] vol. 71, No. 844, Apr. 1998 (Apr. 1998), ISSN: 0007-1285, retrieved from the Internet: url:http://bjr.birjournals.org/cgi/reprint/71/844/413.pdf. [retrieved on Nov. 10, 2009].
Lizzi, Frederic, et al., "Ultrasonic Spectrum Analysis of Tissue Assays and Therapy Evaluation," International Journal of Imaging Systems and Technology, Wiley and Sons, New York, vol. 8, No. 1, (Jan. 1, 1997), pp. 3-10.
Maurer C R et al., Registration of 3-D Images Using Weighted Geometrical Features, IEEE Transactions on Medical Imaging, IEEE Service Center, Piscataway, NJ, US vol. 15, No. 6, Dec. 1, 1996 (14 pages).
Meertens, H. et al. A method for the measurement of field placement errors in digital portal images, Phys. Med. Biol., 1990, vol. 35, No. 3, pp. 299-323.
Mencarelli, et al., "A Dosimetric Method to derive optimal couch corrections in the presence of anatomical deformations for H & N cancer," abstract, 2011, 2 pages.
Nagel, et al., "Online dose-guided setup correction protocol for hypo fractionated lung radiotherapy," abstract, 2009, 1 page.
Reinstein, L. et al. *Radiotherapy Portal Imaging Quality, Report of AAPM Task Group No. 28,* American Association of Physicists in Medicine by the American Institute of Physics, New York, 1988.
Search Report for European Patent Application No. 06790638.8, dated Apr. 23, 2010 (7 pages).
Simpson, R.G. et al. *A 4-MV CT scanner for radiation therapy: The prototype system.* Med. Phys. 9(4), Jul./Aug. 1982, pp. 574-579.
Supplementary European Search Report dated Oct. 30, 2008 for European Patent Application No. 05788508.9/PCT/CA2005001428.
Supplementary European Search Report for PCT/CA2005001106_RNM-003PC_dated Nov. 10, 2009, 6 pages.
Supplementary European Search Report, for PCT Application No. PCT/CA2005001135, dated Feb. 27, 2009 (12 pages).
Supplementary Partial European Search Report for EP Application No. 5763463, dated Nov. 30, 2009, 7 pages.
Swindell, W. et al. *Computed tomography with a linear accelerator with radiotheraphy applications,* Med. Phys. 10(4), Jul./Aug. 1983, pp. 416-420.
Troccaz, J. et al. Conformal external radiotherapy of prostatic carcinoma: requirements and experimental results, Radiotherapy and Oncology 29 (1993) pp. 176-183.
Troccaz., J et al. Patient Setup Optimization for External Conformal Radiotherapy, Journal of Image Guided Surgery, 1, pp. 113-120 (1995).
Van de Geijn, J. et al. *A Graticule for Evaluation of Megavolt X Ray Port Films,* Radiation Oncology Biology Physics, Nov. 1982, vol. 8, No. 11 pp. 1999-2000.
Written Opinion for PCT/CA2005/001106 dated Nov. 15, 2005.
Written Opinion of the International Search report for PCT/CA2005/001105 dated Oct. 27, 2005.
Written Opinion of the International Searching Authority for PCT/CA2005/001428 dated Nov. 8, 2005 (6 pages).
Written Opinion of the International Searching Authority for PCT/CA2006/001289 dated Oct. 30, 2006 (6 pages).

(56) References Cited

OTHER PUBLICATIONS

Written Opinion of the International Searching Authority for PCT/CA2006/001461 dated Dec. 8, 2006 (5 pages).
Written Opinion of the International Searching Authority for PCT/CA2007/000898 dated Jul. 23, 2007 (6 pages).
Zitova, B. et al., Image Registration Methods: A survey, Image and Vision Computing, Elsevier, Guildford, GB, vol. 21, No. 11, Oct. 1, 2003 (24 pages).
Preliminary Report for PCT/CA10/002008, dated Jul. 26, 2012, (5 pages).
International Search Report, issued by the European Patent Office in corresponding Application No. EP 10796634.3, dated Sep. 3, 2013, 7 pp.
Communication Pursuant to Article 94(3) EPC, issued by the European Patent Office in corresponding European Application No. 10 796 634.3, dated Jun. 13, 2017 (6 pages).
"European Application Serial No. 10796634.3, Office Action dated May 8, 2018", 6 pgs.
"European Application Serial No. 10796634.3, Response filed Mar. 31, 2014 to Extended European Search Report dated Sep. 3, 2013", 12 pgs.
"European Application Serial No. 10796634.3, Response filed Nov. 1, 2017 to Communication pursuant to Article 94(3) EPC dated Jun. 13, 2017", 12 pgs.
"European Application Serial No. 18200285.7, Extended European Search Report dated Dec. 14, 2018", 7 pgs.
"European Application Serial No. 8200285.7, Response filed Aug. 20, 2019 to Extended European Search Report dated Dec. 14, 2018", 8 pgs.
"International Application Serial No. PCT/CA2010/001079, International Preliminary Report on Patentability dated Jan. 19, 2012", 8 pgs.
"International Application Serial No. PCT/CA2010/001079, International Search Report dated Oct. 25, 2010", 4 pgs.
"International Application Serial No. PCT/CA2010/001079, Written Opinion dated Oct. 25, 2010", 6 pgs.

\* cited by examiner

ADAPTIVE RADIOTHERAPY TREATMENT USING ULTRASOUND

CROSS-REFERENCE TO RELATED APPLICATIONS

This application claims priority to provisional patent application Ser. No. 61/224,582, entitled "Adaptive Radiotherapy Treatment Using Ultrasound" filed on Jul. 10, 2009, the entire contents of which are incorporated herein by reference.

TECHNICAL FIELD

This invention relates to methods and systems for monitoring therapy treatments, and more specifically to observing the effects of radiation and anatomical changes during radiotherapy treatment fractions.

BACKGROUND INFORMATION

While a patient undergoes radiotherapy treatment, the location, arrangement or shape of anatomical structures or organs can vary relative to the treatment coordinate system being used to delivery the therapy. This is especially true with respect to a planning stage, when a treatment plan is initially devised, and when they are set up for each treatment fraction (commonly referred to as interfractional motion). Furthermore, the anatomy can change during the actually treatment delivery, commonly referred to as intrafractional motion. Having the target tissue move or change shape relative to the treatment plan can cause a deterioration of the actual delivered dose to the target organs and risks exposing surrounding sensitive structures to unwanted radiation.

Due to its excellent soft-tissue contrast, ultrasound imaging is a commonly-used method to obtain images of patient anatomy throughout an entire radiotherapy process. For example, three-dimensional ultrasound (3DUS) images acquired in conjunction with a CT simulation may be used to enhance contouring of structures for planning by fused CT/3DUS images and to form an initial reference image of the internal anatomy for subsequent image guidance. Similarly, 3DUS images acquired in the treatment room, prior to each fraction, may be compared to reference 3DUS images to identify interfractional changes in internal anatomy. These 3DUS images acquired are generated by manually sweeping a 2DUS probe over a region of interest while detecting the position and orientation of the 2DUS probe. A freehand-3DUS image is then constructed relative to a room coordinate system is the imaging or therapy room. The position and orientation of the probe throughout the sweep are commonly found by detection of infrared markers affixed to the probe handle by a calibrated optical camera system.

Although freehand-3DUS imaging is useful for both planning and measuring interfractional motion, there are benefits to leaving the probe in place once the patient is set up in the treatment room, and acquiring either 2DUS or 3DUS images using a non-freehand 3DUS probe using, for example, a mechanically sweeping probe or matrix probe. Images can then be acquired at will, independent of the radiation therapist, without user variability. Multiple images can be acquired before, during, and after treatment to detect intrafractional motion, and changes in target location or shape can be compensated for during delivery of the current treatment fraction and/or in subsequent treatment fractions.

However, due to various constraints these techniques are not technically feasible. One constraint arises from the geometry of treatment and imaging apparatus; an ultrasound probe, for example, generally must maintain contact with the patient while the radiation is being delivered, but in most cases, the probe sits in the path of commonly used beam angles. This will affect the radiation dose distribution inside the patient, which in turn cannot be compensated for standard radiotherapy beams.

Moreover, radiation beams are typically directed at the patient from multiple intersecting directions, and the probe must not be in the path of the radiation beam, which would cause attenuation of the radiation, and potentially increase the skin dose to the patient. Furthermore, a user cannot remain in the radiation room to operate the ultrasound device while the beam is on due to radiation safety concerns. What is needed, therefore, are methods, systems and apparatus that facilitate the use of ultrasound imaging for planning, inter and intrafractional imaging of a patient undergoing radiotherapy treatment while not interfering with the radiation beam and permitting operation without a user in the treatment room, thus allowing for appropriate adjustments to be implemented during treatment delivery, for changes to patient positioning, or in some cases, to halt treatment altogether.

SUMMARY OF THE INVENTION

Embodiments of the invention permit simultaneous use of radiation therapy devices (e.g., a LINAC) and ultrasound imaging probes. To avoid the constraints described above, the radiation and imaging entry points are maintained in mutually exclusive spaces and, in some cases, travel along mutually exclusive paths to the target tissue. In this way, the ultrasound probe can acquire a temporally distinct set of two-dimensional and/or three-dimensional images while the radiation beam is active and administering radiotherapy, in addition to just prior to and after a fraction. This approach to detecting and compensating for intra- and interfractional motion before, during, and after radiotherapy fractions allows for the real-time adaptation of a radiation treatment plan without risking mechanical or electromagnetic interference between the radiotherapy device and the diagnostic imaging device, and avoids potential radiation damage to the ultrasound probe. As a result, it is possible to plan and/or correct for interfractional motion, and particularly intrafractional motion while the probe remains stationary, allowing technicians to remain outside the radiation delivery room.

More specifically, corrections may be implemented by detecting the location and movement of target tissue and surrounding sensitive structures at many points in time before, during and after treatment with little or no direct involvement by a human. As a result, physicians, technicians and radiobiologists can safely and quickly review the effectiveness of radiotherapy or other treatments to determine if treatment modifications are warranted, as well as to document and understand the relationship between dosages and in-vivo damage to diseased cells and surrounding healthy tissue. Deviations from the original plan can be compensated, for example, by moving the treatment couch, stopping the beam if the organ positions are out of tolerance, or modifying the beam delivery parameters such as beam apertures and angles in real time or at various discrete time points throughout the treatment. Compensations can be made during the fraction itself or can be carried out by modifying the treatment plan for subsequent fractions.

In a first aspect of the invention, a method of monitoring radiation treatment being delivered to a patient includes positioning the patient such that a radiation beam is delivered to a lesion within the patient along a beam-delivery path; securing a diagnostic imaging device about the patient such that the diagnostic imaging device does not intersect the beam-delivery path; and simultaneously administering radiation therapy along the beam-delivery path and obtaining diagnostic images using the imaging device.

The diagnostic imaging device may be a two-dimensional ultrasound imaging device, in which case the images reflect changes within the two-dimensional plane being acquired. In some cases, the diagnostic imaging device is a three-dimensional ultrasound imaging device, which can capture fully-formed three-dimensional images, or, in some cases, multiple two-dimensional slices from varying angles or positions. These slices may then be reconstructed into three-dimensional images. In either case, the ultrasound imaging device may include one or more tracking devices (typically reflectors or emitters attached to the handle or head of the device) which allow for real-time positional tracking of the device. By tracking the device over time, the multiple temporally-displaced, three-dimensional ultrasound images may be used to create a "four-dimensional" ultrasound image.

In some embodiments, the diagnostic imaging device can be secured into a brace, thereby ensuring that the diagnostic imaging device does not intersect the beam-delivery path, and/or the sonifications emitted by the diagnostic imaging device do not substantially interfere with the beam-delivery path. For example, the lesion may be a prostate tumor, in which case the diagnostic imaging device is positioned transperineally. In some implementations, a comparison of diagnostic images taken during the delivery of radiation therapy may indicate the need for an adjustment of certain radiation treatment parameters such as the beam angle, beam isocenter, couch position, beam apertures, beam delivery, focal point, energy level, or duration of the fraction. In certain cases, a baseline diagnostic image of the lesion (i.e., an image taken prior to the delivery of radiation therapy or during the treatment planning stage) is also used in the comparison process. The baseline images may be ultrasound images and/or CT images. Additional diagnostic images may also be obtained just prior to and/or immediately after delivery of radiation, but while the patient remains in the treatment position.

In another aspect of the invention, an apparatus for monitoring the delivery of radiation treatment being delivered to a patient includes an imaging device (e.g., a two or three-dimensional ultrasound imaging device) and a brace for holding the device. The brace includes a housing for accepting the imaging device and may be secured to a patient support platform (e.g., a table) such that the brace and the diagnostic imaging device remain outside of a radiation treatment beam as radiation treatment is delivered to the patient. As a result, the diagnostic imaging device obtains images during, but without interfering with, the delivery of radiation to the patient.

The ultrasound imaging device may also include one or more optical tracking devices which facilitate real-time positional tracking of the imaging device by a room-based laser tracking system, for example. As the diagnostic images are obtained and analyzed, adjustments to certain radiation treatment parameters (e.g., the beam angle, entry point, focal point, energy level, etc.) may be implemented. The position of the brace may be adjustable (either manually or automatically) in response to the changes in the parameters.

In another aspect, a system for monitoring the delivery of radiation therapy includes a diagnostic imaging device for obtaining diagnostic images as radiotherapy treatment is delivered to a patient, a register for storing the images, and a processor. The processor is configured to compare two or more of the diagnostic images and determine adjustments to radiation treatment parameters based on the comparison. The comparison may be done by automatically segmenting the target anatomy and other nearby critical structures in each image, or, in some instances, by comparing grayscale values to identify differences in a patient's anatomy over time.

The system may also include a brace that ensures the diagnostic imaging device does not interfere with a beam-delivery path of the radiotherapy treatment. A controller may be used to cause the brace to move according to the new radiation treatment parameters, such as if a new beam angle and/or entry point are to be used. A monitor may be used to display the radiation treatment parameters and, in some cases, the diagnostic images. A baseline diagnostic scan may also be used (and, in some cases, stored in the register) as input into the comparison process.

In another aspect, the invention provides software in computer-readable form for performing the methods described herein.

BRIEF DESCRIPTION OF FIGURES

In the drawings, like reference characters generally refer to the same parts throughout the different views. Also, the drawings are not necessarily to scale, emphasis instead generally being placed upon illustrating the principles of the invention.

DETAILED DESCRIPTION

Throughout the following descriptions and examples, the invention is described in the context of monitoring changes to patient anatomy during treatment delivery, and/or monitoring and measuring the effects of radiotherapy as administered to a lesion or tumor. However, it is to be understood that the present invention may be applied to monitoring various physical and/or biological attributes of virtually any mass within or on a patient in response to and/or during any form of treatment. For example, the therapy can include one or more of radiation, cryotherapy, or any other treatment method.

Figure 1:
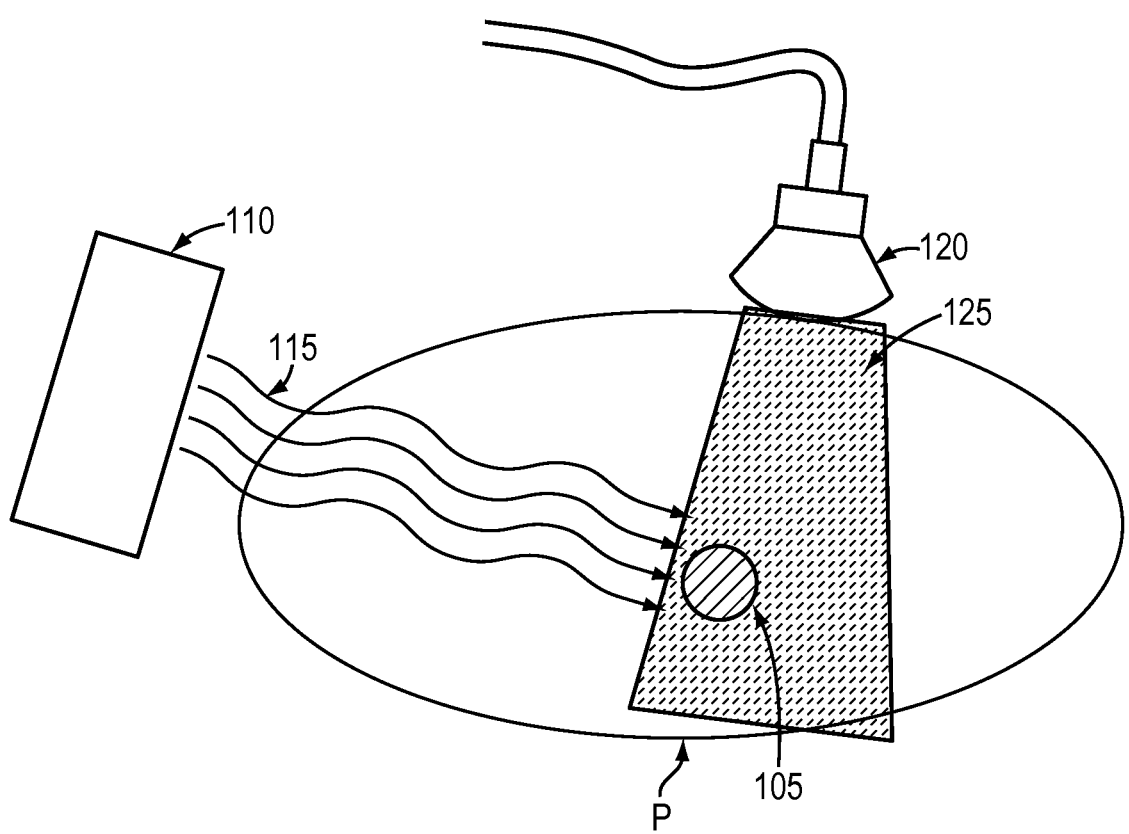
FIG. 1 is a schematic diagram illustrating the use of a diagnostic imaging device to obtain images of a lesion during the administration of radiation therapy in accordance with one embodiment of the invention.

Referring to FIG. 1, one or more ultrasound scans are acquired during the delivery of radiotherapy treatment, which is typically given in many fractions over an extended period of time. For example, an ultrasound scan is taken of a target organ or lesion 105 within the illustrated region R of the patient. Radiotherapy treatment is administered to the lesion 105 using, for example, an external single-beam conformal radiation device 110 that can be rotated around the patient to deliver radiation 115 from various angles. In other embodiments, a multi-beam device may be used. The scans can be taken in one, two, or three dimensions to obtain ultrasonic data, using, for example, a hand-held ultrasonic scanning device 120. Unlike conventional techniques where the scanning is limited to just following the administration of a new radiotherapy fraction, just prior to a fraction, or at some other time between fractions, the scans in accordance herewith may also be taken at the same time the radiation is being delivered to the lesion 105.

Figure 2:
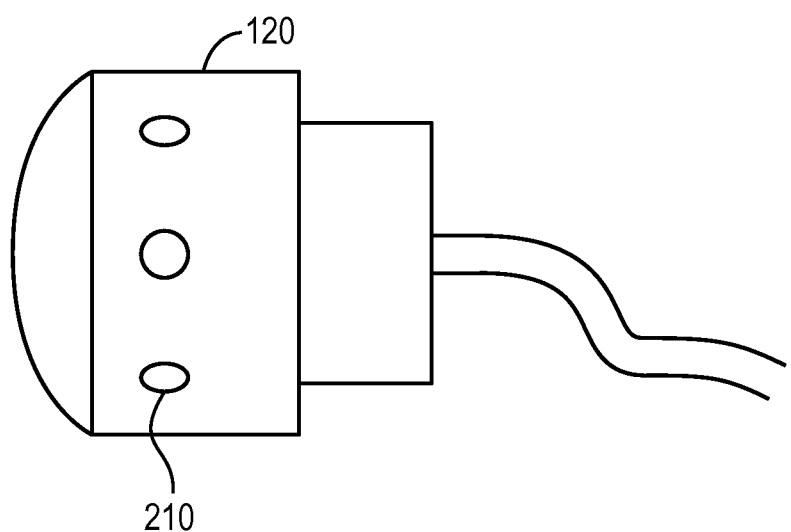
FIG. 2 is a schematic diagram of a hand-held imaging device including tracking markers to facilitate obtaining positional information in accordance with one embodiment of the invention.

However, in order to ensure accuracy of the scan(s), proper administration of the radiation, and safety of the operators, the scanning device is positioned in a manner that does not interfere with the beam angle (including the beam entry point) while still providing clear, accurate and consistent images of the lesion. Further, in some implementations, tracking markers (e.g., reflectors, emitters or other devices) may be placed about the scanning device to locate and track the device with respect to one or more coordinate systems. For example, FIG. 2 illustrates three markers 210 placed atop an ultrasound device, which may be used in conjunction with a conventional marker-based, optical, magnetic and/or audio tracking system.

By sensing signals transmitted from the emitters 210 located about the device 120, the tracking system may calculate (using standard triangulation methods) and record the location of the portable device 120 as its position moves with respect to the signal-receiving unit of the tracking system. This position data may be communicated to the operator of the portable device, thus allowing the operator to accurately locate the portable device at any position with respect to the receiver of the tracking system. Alternatively, position data may be provided to a controller that automatically adjusts the position of the device 120. The position data may be communicated through a visual display, audio signal, or combination of the two. The emitters 210 may be permanently attached to the device 120, and/or releasably attached to the portable device.

In one particular implementation, the tracking system is located at a fixed location within or surrounding a separate defined coordinate system. For example, the tracking system may include one or more receiving units placed on or mounted to the walls of a room, with a coordinate system defined by the walls of the room. As such, the tracking system can convert the detected position of the portable device from a location in the tracking system's coordinate system to a location in the room coordinates (or, in some cases, a treatment-device based coordinate system). This allows the device 120 to be accurately positioned and oriented with respect to any tracked location within the room and/or the patient.

The tracking system and/or the room may be defined by a Cartesian coordinate system, a cylindrical coordinate system, and/or a spherical coordinate system. For example, in one embodiment of the invention, the tracking system calculates the location of the portable device with respect to a receiving unit in spherical coordinates, and then converts this position into a location within a room defined by Cartesian coordinates. The (x, y, z) axes of the room-based Cartesian coordinate system may correspond, for example, to the floor and walls of the room, to a coordinate system whose center (i.e., the (0, 0, 0) location) is positioned either at a corner of the room or at some other point within the room. In one embodiment, the center of a treatment room-based Cartesian coordinate system is located at the isocenter of the linear accelerator, which is the point about which radiation beams from all directions intersect and is located at a known fixed position in the room. Thus, the tracking system can allow a user to position a portable device accurately with respect to the treatment isocenter, allowing for improved medical diagnosis and treatment using portable devices.

While the discussions above and following describe the use of an ultrasound imaging apparatus during the delivery of radiotherapy, similar techniques and systems may also be used in conjunction with other imaging modalities, such as in a CT scanning room. Such uses may include applications during a treatment simulation and/or treatment planning, wherein the ultrasound device does not interfere with potential virtual treatment beams which will be planned based on the CT images. As a result, a baseline, planning-stage image may be acquired for future use in the treatment room. Moreover, an ultrasound image may be captured immediately during CT scanning, either by synchronizing ultrasound acquisition with the CT, or in the alternative, using a radiation-sensing device that senses when the CT beam is on and triggers the capture of ultrasound images. In some embodiments, multiple ultrasound images can be acquired throughout the CT imaging session (as opposed to a radiotherapy treatment session) to quantify internal motion during the session. Alternatively, the acquisition of ultrasound images can be correlated with 4DCT images such that a temporal series of CT and ultrasound images correspond to each throughout the imaging session. In either case, the apparatus and techniques described herein allow for real-time or near-real time imaging in instances in which the operator cannot be in the treatment or CT imaging room to adjust or hold the ultrasound device.

In general, the methods, apparatuses, and systems described herein may be implemented at various stages of radiation treatment. For example, during the planning stage, 3DUS or 4D ultrasound may be fused with other imaging data (e.g., CT scan data) to provide enhanced radiation treatment planning images. More specifically, a non-ultrasound imaging device may be used to provide a first set of imaging data that is associated with a specific, fixed frame of reference. Typically, this would be either a coordinate system associated with the imaging device itself, or, in other cases, the room itself.

The ultrasound device is then used to capture a second set of imaging data. This second set may include a series of 2D image slices acquired at a different positions relative to the patient. The image different positions may be achieved using a single probe rotatably mounted within a probe casing such that the entire assembly can rotate about an axis, or, in some cases, the probe can sweep along one access within the casing to obtain images from different directions. In some instances the probe may be moveable relative to the patient, allowing a single 2D probe to be used to acquire multiple image slices. As described above, the probe may also be mounted on a moveable brace which maintains the probe position such that it does not interfere with the CT imaging process. The 2D image slices may then be used to construct a 3D image volume.

During the ultrasound imaging process, position data is captured for each 2D image slice as it is acquired. In implementations in which the ultrasound probe is encased in a housing, the position of the housing is determined, and registered with the position of the probe within the housing.

Using the housing position data, the mechanical position data of the 2D image slices within the housing, and the ultrasound imaging data, a 3D volumetric ultrasound image is constructed relative to a second fixed frame of reference, corresponding to a converted set of image data in the second fixed frame of reference. The converted image data is then combined with at least some of the first set of imaging data, using both the first and second fixed frames of reference to provide a composite set of imaging data to be used in developing a treatment plan. In some instances the two frames of references may be the same coordinate system, but in many implementations they are distinct.

Similar techniques may also be used to compare images acquired just prior to treatment delivery to images taken during the planning stage. In such implementations, reference structures are identified in the composite imaging data and a third set of images is captured. As with in the planning stage, an ultrasound device may be used to capture a series of 2D image slices, each being acquired at different mechanical positions. These images, taken using the same imaging modality and using the same imaging technique, can then be compared to each other to determine shifts and movement of the target anatomy that may have occurred between the planning process and just prior to treatment delivery. More specifically, the reference structures may be identified in the images taken just prior to treatment and compared to the corresponding structures in the planning stage images. Based on any changes, the treatment plan may be modified (e.g., adjust the couch position, change the beam angles, etc.) immediately prior to delivery of radiation treatment.

In yet another implementation, embodiments of the invention may be used during delivery of radiation therapy. In these cases, the third set of images described above are acquired at the same time that radiation is delivered to the patient. As described above, position data is determined for the casing corresponding to each 2D image slice as it is acquired, and using the position data, the mechanical position data of the probe within the casing, the location of the structures within the 2D data (or, in some cased, reconstructed 3D data) can be determined at discrete points in time throughout treatment. The locations of the structures in the third image set can be compared to the locations in the images taken during treatment planning, just prior to treatment delivery, and/or prior images taken during the treatment to determine to identify structure motion during treatment, modify the treatment plan in real-time, or in some cases, halt treatment altogether.

The techniques and system described herein may be used in conjunction with the planning and administration of radiation treatment therapy to any number of anatomical locations. Two specific applications are described in greater detail below.

Figure 3:
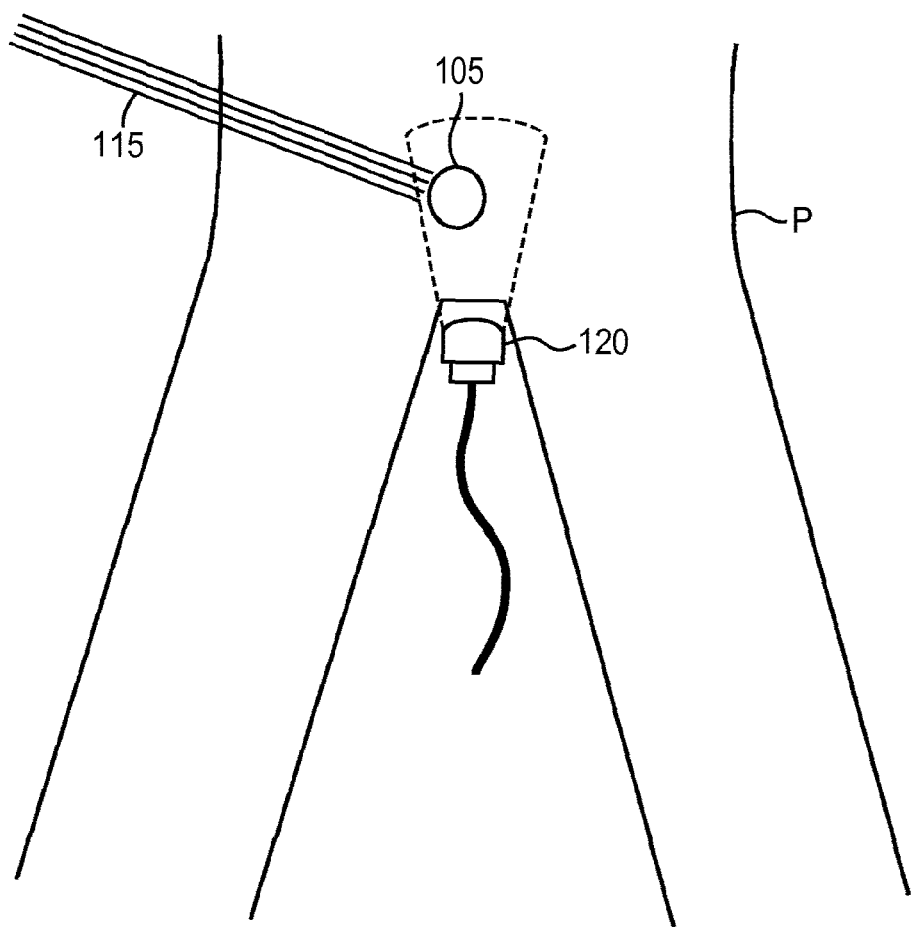
FIG. 3 is a schematic diagram illustrating the use of a hand-held imaging device in a transperineal application to obtain images of a lesion during the administration of radiotherapy to a lesion near the prostate gland in accordance with one embodiment of the invention.

In FIG. 3, the lesion 105 is located in or near the prostate gland of patient P. In radiology, the prostate is typically imaged trans-rectally. This approach, however, is not preferred for image-guided radiotherapy (IGRT) because it can deform the prostate and is not practical for many treatment sessions. Furthermore, the proximity of the diagnostic device to the prostate may also affect the distribution of the radiation about the treatment area. Moreover, while interfractional IGRT uses transabdominal imaging, this approach places the probe in the path of the radiation beam. In order to properly treat the prostate, the radiotherapy 115 is delivered while the patient P lies on a table and the treatment device (typically an external, single-beam conformal radiation device, or in some cases a multi-beam device) rotates about the patient's frontal anatomy. In doing so, the entire area above the patient is effectively "off limits" to any other devices (and certainly to any personnel who operate such devices). As such, the diagnostic device 120 may be placed in a transperineal position between the patient's legs and directed towards the lesion 105. In positioning the device in this manner, the device itself, and, does not interfere with the radiation beam as it travels to the lesion 105. This allows diagnostic images to be obtained at the same time the radiation therapy is delivered, meaning organ movement occurring within or around the lesion and/or cell damage can be monitored during treatment, and real-time or quasi-real-time intrafraction adjustments may be made.

For example, if, during a treatment session, the prostate shifts in position (due, for example to the filling of the bladder, breathing, flatulence, or other patient movement) the new location will be indicated on the diagnostic images. The beam shape, entry point, intensity level, focal point, beam isocenter, couch position, beam apertures, beam delivery or other parameter may then be adjusted accordingly. In other instances the target make change shape, such as the uterus changing shape as the bladder fills, which may also require new treatment parameters. In some embodiments, a baseline (e.g., pre-fraction) scan may be obtained and used in conjunction with the intrafractional images to determine the necessary parameter adjustments. Further adjustments may be based on comparisons with images taken just prior to and/or following treatment delivery.

In another example, the diagnostic imaging probe may be placed on one quadrant of a breast to obtain images of a lumpectomy cavity therein, while the radiation beam is directed to enter from an adjacent quadrant, thus not interfering with the probe. In some instances where multiple beam angles are necessary, the treatment may be stopped so that the probe can be moved to another quadrant, and the radiation beam can then be delivered from a new adjacent quadrant. These steps may be repeated as many times as necessary to deliver the prescribed radiation dosage.

Figure 4:
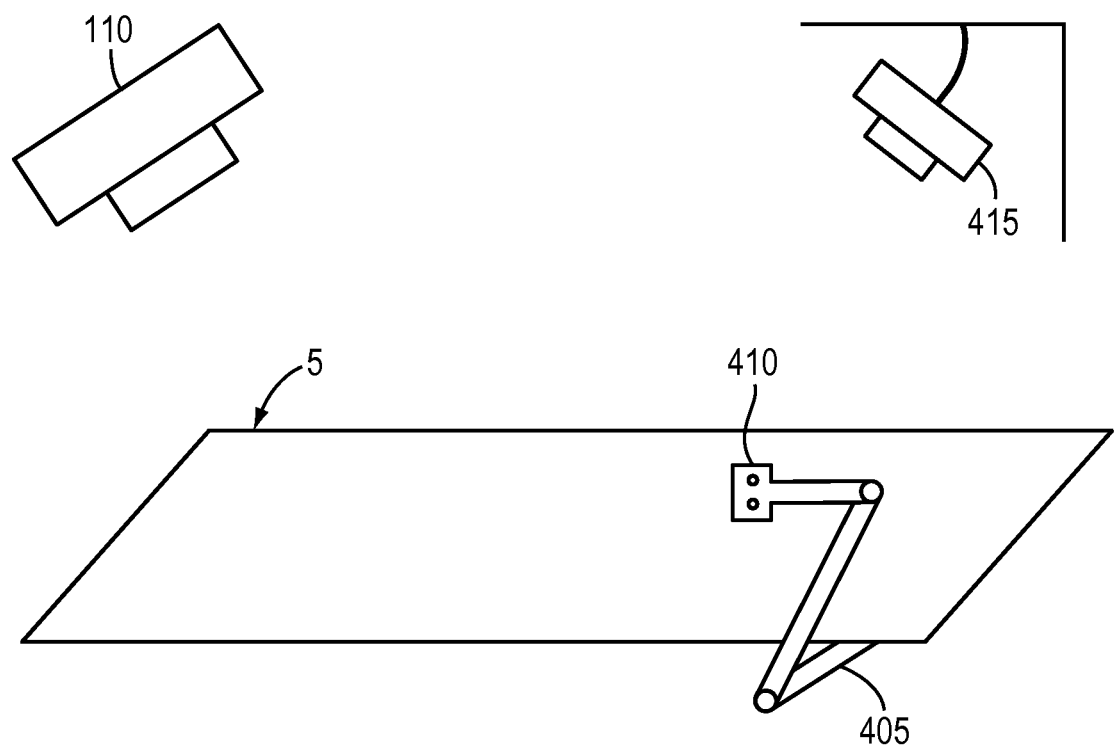
FIG. 4 is an illustration of a treatment room in which the invention may be implemented and used.

In certain cases, the diagnostic probe may require a suitable mechanical structure (i.e., a brace) to hold it in place during use. This allows the user to be outside of the radiation treatment room while the radiation beam is in use, which is important for safety reasons. Referring to FIG. 4 as an example, a brace 405 may be fastened or otherwise connected to a stationary structure (e.g., the floor, a bracket, the wall, etc.) or, in some cases, attached to a patient support device S such as a bed or examination table. The brace 405 may include a housing 410 having a cooperating, mating structure for accepting the imaging device such that the probe remains locked into place during use. In some instances, the brace 405 includes one or more hinges or other joints that permit the movement of the brace around the patient. For example, the brace may be rotatably attached to the bed and include joints that, together, allow for six degrees of movement freedom. In some instances, the brace may be automatically and/or remotely controlled such that the imaging probe can be moved about the patient without requiring an operator to be physically present (e.g., the operator may be in an adjacent room, shielded from the radiation). In other instances, the housing itself may rotate in one or two directions, thus allowing the probe to "sweep" across the patient, thus acquiring images from different angles.

In some embodiments, the brace may be used to secure the ultrasound probe during a treatment planning session to acquire images during the treatment planning session from approximately the same direction that the probe will be located when used during treatment delivery. These images may be used for planning purposes as an initial reference for future images acquired in the treatment room. Although no radiation is delivered during the planning session, it is beneficial to maintain the same imaging setup from planning to treatment, and to have the probe remain out of the beam path while secured in approximately the same position during treatment delivery. In other instances, the brace may be used during treatment sessions but not at the same time as radiation is delivered to the patient. This allows the probe to remain in a known, stable position outside the beam throughout an entire fraction without needing adjustment by a technician.

Figure 5:
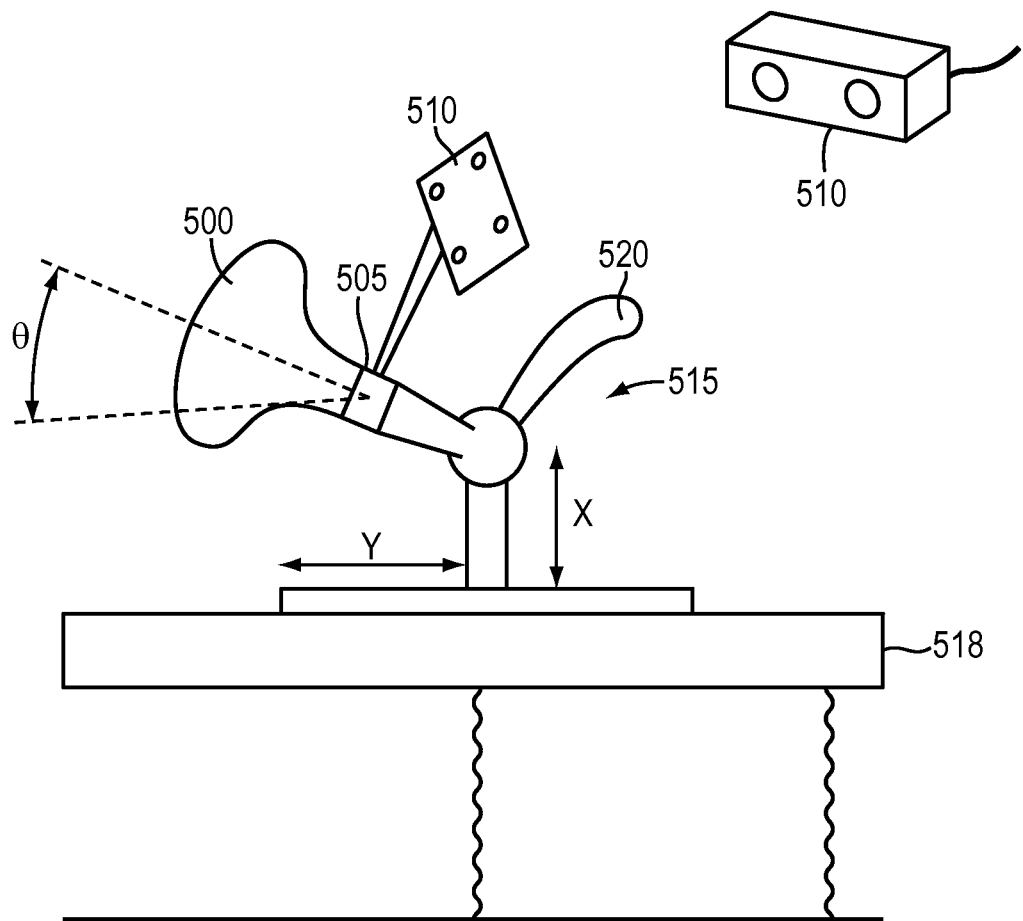
FIG. 5 is an illustration of a brace according to one embodiment of the invention.

FIG. 5 illustrates one embodiment of a brace which is particularly useful for transperineal imaging of the prostate. A probe 500, preferably a 3DUS probe, has a handle 505 with infrared markers affixed in such a way as to be visible by an optical camera 510. The brace 515 is affixed to the treatment couch 518 and adjustable such that the angle θ of the probe as well as its height (illustrated as the x axis) with respect to the table can be easily adjusted to obtain a good view of the prostate and surrounding structures through the perineum. The location and/or position of the probe can also be adjusted with respect to the patient (illustrated as the y axis) so the probe touches the patient's perineum with sufficient contact to achieve accurate imaging but without exerting too much pressure. As such, the brace allows movement of the probe according to one, two or three degrees of freedom with respect to the patient. In some embodiments, a handle 520 aids the user in adjusting the probe in the x, y and/or θ directions without touching the patient or the probe itself. The probe position can be locked into place once all adjustments are made with the brace using a latch, clip, pin, or other securing means. In some embodiments, the x, y and θ parameters can be adjusted remotely without human contact using a remotely-controlled motor or actuator assembly, based either on visual inspection of the image or by a priori knowledge of the prostate position.

In some cases, the ultrasound images are fully formed "b-mode" images that include pixel values related to the anatomy and boundaries, which may be used to monitor geometric organ motion. In other cases, the ultrasound signal itself (sometimes referred to as "RF data") may also be used to monitor characteristics of the organ being treated. For example, features of the RF data can be extracted from the signal to characterize tissue types (e.g., bone, fat, muscle, etc.) and/or determine tissue damage caused by radiation, in some cases even while the treatment is being delivered. More specifically, by calculating the power spectrum of the RF data reflected from a region of interest (or, in some cases, on a pixel by pixel basis), spectrum features such as the slope and intercept can be used as an indicator of tissue type and whether the region of interest contains cancerous cells. When comparing to an initial baseline from a previous image, changes in the RF data characteristics can provide an indication as to the effectiveness of treatment.

The technique is applicable not only to radiation therapy but to any other therapy which leads to tissue damage, e.g., the immediate or eventual killing of cells. Such therapies can include, for example, chemotherapy, cryotherapy, single-fraction radiosurgery, hyperthermia, or brachytherapy, or any combination of these treatment methods. Comparisons among scans taken during the delivery of tissue-damaging therapy provide a direct measurement of the effectiveness of the treatment in both time and space, allowing the physician to adapt the treatment based on the results.

Figure 6:
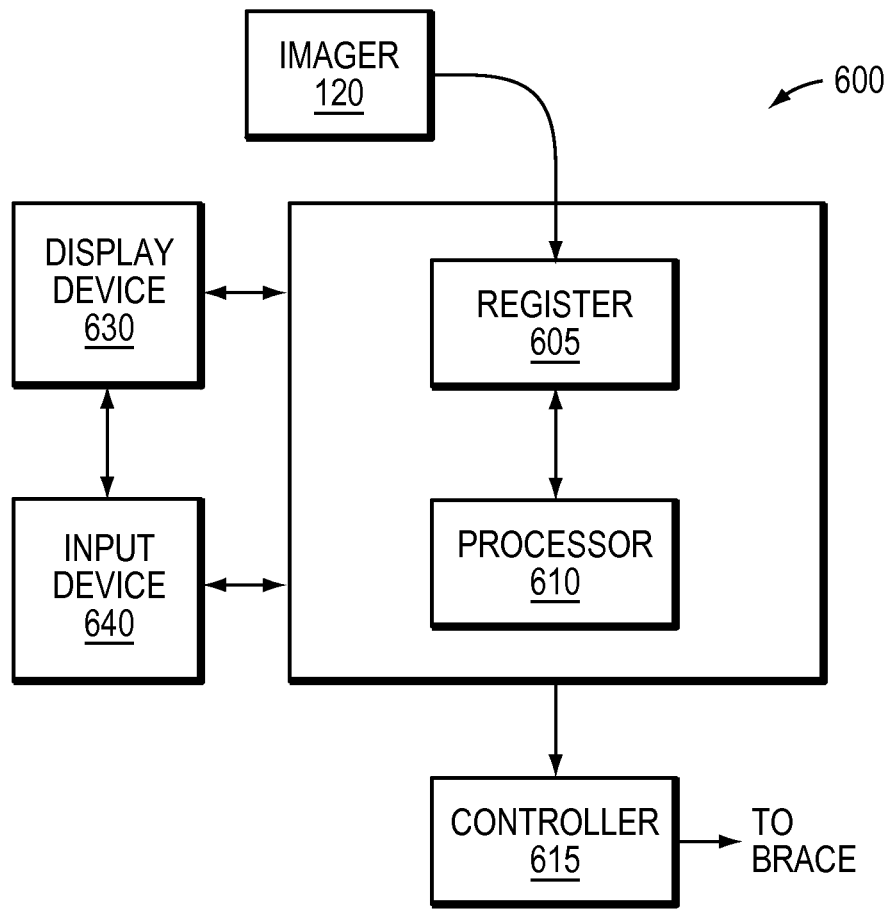
FIG. 6 is a schematic illustration of an adaptive radiotherapy treatment monitoring system according to an embodiment of the invention.

Referring to FIG. 6, one embodiment of a system 600 for performing the techniques described above includes a register 605 or other volatile or non-volatile storage device that receives image data from an imaging device 120 (such as an ultrasound device) via a cord or wire, or in some embodiments via wireless communications. The system also includes a processor 610 that, based on the image data and comparisons among the images, uses the techniques described above to adjust and implement new radiation parameters in real-time as the radiation is being delivered to the patient. In some embodiments, the system also includes a controller 615 that, based on the results of the comparisons, implements positional adjustments to the brace. A display 630 and an associated user interface (not shown) may also be included, thus allowing a user to view and manipulate the diagnostic images and/or treatment parameters. The display 630 and user interface can be provided as one integral unit or separate units (as shown) and may also include one or more user input devices 640 such as a keyboard and/or mouse. The display 630 can be passive (e.g., a "dumb" CRT or LCD screen) or in some cases interactive, facilitating direct user interaction with the images and models through touch-screens (using, for example, the physician's finger as an input device) and/or various other input devices such as a stylus, light pen, or pointer. The display 630 and input devices 640 may be in location different from that of the register 605 and/or processor 610, thus allowing users to receive, view, and manipulate images in remote locations using, for example, wireless devices, handheld personal data assistants, notebook computers, among others.

In various embodiments the register 605 and/or processor 610 may be provided as either software, hardware, or some combination thereof. For example, the system may be implemented on one or more server-class computers, such as a PC having a CPU board containing one or more processors such as the Pentium or Celeron family of processors manufactured by Intel Corporation of Santa Clara, Calif., the 680×0 and POWER PC family of processors manufactured by Motorola Corporation of Schaumburg, Ill., and/or the ATHLON line of processors manufactured by Advanced Micro Devices, Inc., of Sunnyvale, Calif. The processor may also include a main memory unit for storing programs and/or data relating to the methods described above. The memory may include random access memory (RAM), read only memory (ROM), and/or FLASH memory residing on commonly available hardware such as one or more application specific integrated circuits (ASIC), field programmable gate arrays (FPGA), electrically erasable programmable read-only memories (EEPROM), programmable read-only memories (PROM), programmable logic devices (PLD), or read-only memory devices (ROM). In some embodiments, the programs may be provided using external RAM and/or ROM such as optical disks, magnetic disks, as well as other commonly storage devices.

For embodiments in which the invention is provided as a software program, the program may be written in any one of a number of high level languages such as FORTRAN, PASCAL, JAVA, C, C++, C#, LISP, PERL, BASIC or any suitable programming language. Additionally, the software can be implemented in an assembly language and/or machine language directed to the microprocessor resident on a target device.

It will therefore be seen that the foregoing represents an improved method and supporting system for monitoring the biological effects of radiotherapy and natural anatomical changes over the course of a treatment regimen. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed. Moreover, although the above-listed text and drawings contain titles headings, it is to be understood that these title and headings do not, and are not intended to limit the present invention, but rather, they serve merely as titles and headings of convenience.

The invention claimed is:

1. A method of monitoring a target tissue in a patient during a radiation treatment, comprising:
    positioning an ultrasound imaging device such that the ultrasound imaging device is in contact with the patient's perineum;
    using the ultrasound imaging device to scan, transperineally, a target tissue in a genitourinary region of the patient to obtain, prior to a radiation fraction, a baseline image of the target tissue and surrounding tissue;
    delivering the radiation fraction along at least one beam-delivery path to the target tissue using a radiation therapy device, wherein the at least one beam-delivery path is directed to the patient's anatomy in a non-transperineal direction;
    simultaneously delivering the radiation fraction while obtaining a plurality of ultrasound images using the ultrasound imaging device, wherein the ultrasound imaging device is positioned to obtain, from at least one transperineal direction, the plurality of ultrasound images, such that the ultrasound imaging device does not intersect the at least one beam-delivery path while obtaining the plurality of ultrasound images;
    comparing the one or more of the plurality of ultrasound images with the baseline image; and
    determining intrafractional movement of at least one of the target tissue or the surrounding tissue based on the compared one or more ultrasound images as the radiation fraction is delivered to the patient by the radiation therapy device.

2. The method of claim 1, wherein obtaining the plurality of ultrasound images comprises obtaining at least one two-dimensional ultrasound image.

3. The method of claim 1, wherein obtaining the plurality of ultrasound images comprises obtaining at least a three-dimensional ultrasound image.

4. The method of claim 3, wherein the ultrasound imaging device further comprises one or more tracking devices to facilitate real-time positional tracking of the ultrasound imaging device.

5. The method of claim 4, further comprising combining a plurality of temporally-displaced three-dimensional ultrasound images to create a four-dimensional ultrasound image.

6. The method of claim 1, wherein the ultrasound imaging device is movable within a predetermined envelope to obtain the plurality of ultrasound images from different respective locations.

7. The method of claim 6, wherein the ultrasound imaging device is attached to a brace, connected to a stationary structure, for holding the ultrasound imaging device at each of the different locations.

8. The method of claim 7, further comprising adjusting a position of the brace in response to a change in one or more radiation treatment parameters.

9. The method of claim 8, wherein the one or more radiation treatment parameters comprises at least one of a beam angle, a beam isocenter, a couch position, a beam aperture, a beam delivery path, a focal point, an energy level, or a duration of a radiation fraction.

10. The method of claim 7, further comprising rotating the brace such that the ultrasound imaging device can obtain ultrasound images of the genitourinary region of the patient, at each of the different locations, during delivery of the radiation fraction by the radiation therapy device.

11. The method of claim 1, wherein the target tissue comprises a prostate tumor.

12. The method of claim 1, wherein the ultrasound imaging device is movable within an envelope such that sonications emitted by the ultrasound imaging device do not substantially interfere with the radiation delivered by the radiation therapy device along the at least one beam-delivery path.

13. The method of claim 1, further comprising comparing two or more of the plurality of ultrasound images obtained during the simultaneous delivery of the radiation fraction by the radiation therapy device and adjusting one or more radiation treatment parameters based on the comparison.

14. The method of claim 13, wherein the one or more radiation treatment parameters comprises at least one of a beam angle, a beam isocenter, a couch position, a beam aperture, a beam delivery path, a focal point, an energy level, or a duration of a radiation fraction.

15. The method of claim 1, wherein the genitourinary region of the patient comprises at least one of a prostate, a tumor, a bladder, or a lesion.

16. The method of claim 1, wherein positioning the ultrasound imaging device comprises positioning the ultrasound imaging device between the patient's legs.

* * * * *